(12) United States Patent
Bachmaier et al.

(10) Patent No.: US 8,168,176 B2
(45) Date of Patent: May 1, 2012

(54) CBLB FOR TREATING ENDOTOXIN-MEDIATED DISORDERS

(75) Inventors: Kurt Bachmaier, Chicago, IL (US); Asrar B. Malik, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 49 days.

(21) Appl. No.: 12/514,410

(22) PCT Filed: Nov. 12, 2007

(86) PCT No.: PCT/US2007/084430
§ 371 (c)(1),
(2), (4) Date: Jul. 2, 2009

(87) PCT Pub. No.: WO2008/063957
PCT Pub. Date: May 29, 2008

(65) Prior Publication Data
US 2010/0061970 A1 Mar. 11, 2010

Related U.S. Application Data

(60) Provisional application No. 60/857,831, filed on Nov. 10, 2006.

(51) Int. Cl.
*A61K 38/00* (2006.01)
*A61P 31/00* (2006.01)
*C07K 1/00* (2006.01)
*C07H 21/04* (2006.01)

(52) U.S. Cl. .......... 424/94.5; 514/1.1; 514/1.4; 514/2.1; 514/12.2; 530/350; 536/23.2

(58) Field of Classification Search .................. 424/94.5; 514/1.1, 1.4, 2.1, 12.2; 530/350; 536/23.2
See application file for complete search history.

(56) References Cited

U.S. PATENT DOCUMENTS

| 6,087,122 | A | 7/2000 | Hustad et al. |
| 6,258,601 | B1 | 7/2001 | Monia et al. |
| 6,706,505 | B1 * | 3/2004 | Han et al. .................. 435/183 |
| 7,220,547 | B2 | 5/2007 | Han et al. |
| 2004/0037822 | A1 | 2/2004 | Majetschak et al. |
| 2006/0160869 | A1 | 7/2006 | Singh et al. |

FOREIGN PATENT DOCUMENTS

WO WO-01/23585 4/2001

OTHER PUBLICATIONS

Alves-Filho et al., Toll-like receptor 4 signalling leads to neutrophil migration impairment in polymicrobial sepsis. Crit Care Med., 2006, vol. 34 (2): 461-470.*
Beutler et al. Sepsis and evolution of immune response. Crit Care Med., 2001, vol. 29 (7) (Suppl.): S2-S7.*
Chuang et al., Triad3A, an E3 ubiquitin-protein ligase regulating Toll-like receptors. Nature Immunology, 2004, vol. 5 (5): 495-502.*
Jeon et al. Essential role of the E3 ubiquitin ligase Cbl-b in T cell anergy induction. Immunity, 2004, vol. 21: 167-177.*
Bachmaier, et al. "E3 ubiquitin ligase Cblb regulates the acute inammatory response underlying lung injury," Nature Medicine 13(8):920-926 (2007).
Chang et al. "The E3 Ubiquitin Liagse Itch Couples JNK Activation to TNFα-induced Cell Death by Inducing c-FLIP$_L$ Turnover," Cell 124:601-613 (2006).
Lin, et al. "The role of E3 ligases in autoimmunity and the regulation of autoreactive T cells" Current Opinion in Immunology, 19(6):665-673 2007.
Oh, et al. "Cb1-b Acts as a Gatekeeper to Control OVA-Induced Lung Inflammation," Journal of Allergy and Clinical Immunology, 121(2):S150 (2008).
Bachmaier, et al. "Negative regulation of lymphocyte activation and autoimmunity by the molecular adaptor Cbl-b," Nature 403:211-216 (2000).
Chiang, et al. "Cbl-b regulates the CD28 depedence of T-cell activation," Nature 403:216-220 (2000).
Heissmeyer, et al. "Calcineurin imposes T cell unresponsiveness through targeted proteolysis of signaling proteins," Nature Immunology, 5(3):255-265 (2004).
Meng, et al., "Structure of the amino-terminal domain of Cbl complexed to its binding site on ZAP-70 kinase," Nature 398:84-90 (1999.).

* cited by examiner

*Primary Examiner* — Ganapathirama Raghu
(74) *Attorney, Agent, or Firm* — Marshall, Gerstein & Borun LLP

(57) ABSTRACT

Methods of treating endotoxin-mediated disorders are provided.

8 Claims, 7 Drawing Sheets

CBLB FOR TREATING ENDOTOXIN-MEDIATED DISORDERS

The invention was supported by funding from the National Institutes of Health grant numbers HL077806; HL060678; and HL007829. The government has certain rights in the invention.

CROSS-REFERENCE TO RELATED APPLICATIONS

This application is a U.S. National Phase of International Application No. PCT/US2007/084430 filed Nov. 12, 2007, incorporated herein by reference, which claims the benefit of prior U.S. provisional application no. 60/857,831 filed Nov. 10, 2006, hereby incorporated by reference in its entirety.

FIELD OF THE INVENTION

The invention relates to methods of preventing or ameliorating an endotoxin-mediated disorder.

BACKGROUND

Sepsis is an endotoxin-mediated disorder and the most common cause of acute lung injury (ALI) (MacCallum and Evans, (2005) Current Opinion In Critical Care 11: 43-49), a syndrome with a high mortality rate (Rubenfeld et al., (2005) New England Journal Of Medicine 353: 1685-1693; Levy et al., (2005) Critical Care 9: R502-R507.2, 3). Sepsis is a systemic reaction characterized by arterial hypotension, metabolic acidosis, decreased systemic vascular resistance, tachypnea and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "bacteremia" includes occult bacteremia observed in young febrile children with no apparent foci of infection. The term "sepsis" also encompasses fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) may be caused by a number of organisms. The systemic invasion of microorganisms presents two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (i.e., septic shock) and oftentimes, death.

Cbl proteins have evolutionarily conserved roles in regulating protein tyrosine kinases (Thien and Langdon, (2001) Nature Reviews Molecular Cell Biology 2: 294-305), down-regulating activated receptor tyrosine kinases (Levkowitz et al., (1998) Genes & Development 12: 3663-3674; Yoon et al., (1995) Science 269: 1102-1105; Haglund and Dikic, (2005) EMBO Journal 24: 3353-3359; Haglund et al., (2003) Nature Cell Biology 5: 461-466), and removing activated antigen receptors from the cell surface (Naramura et al., (2002) Nature Immunology 3: 1192-1199). E3 ubiquitin-protein ligase Casitas B-lineage lymphoma proto-oncogene b (Cblb), in particular, regulates adaptive immunity by setting activation thresholds of mature lymphocytes (Chiang, et al., (2000) Nature 403: 216-220; Bachmaier et al., (2000) Nature 403: 211-216; Krawczyk et al., (2000) Immunity 13: 463-473), and is necessary for the induction of T cell tolerance (Jeon et al., (2004) Immunity 21: 167-177). Toll-like receptors (TLRs) are pattern-recognition receptors that have evolved to protect their possessors from microbial infection (Janeway and Medzhitov, (2002) Annual Review Of Immunology 20: 197-216), and TLRs are important for the induction of adaptive immune responses (Takeda et al., (2003) Annual Review Of Immunology 21: 335-376). TLRs also mediate, however, the adverse effects of microbial infection. For example, endotoxins of gram-negative bacteria (lipopolysaccharide (LPS)) signaling through TLR4 cause inflammation resulting in ALI (Beutler and Poltorak, (2001) Critical Care Medicine 29: S2-S6). LPS is the major component of the outer membrane of gram-negative bacteria and is responsible for many of the pathophysiological effects observed during infections with gram-negative pathogens that may lead to septic shock and death (E. T. Rietschel et al., (1992) Scient. Amer. 267: 54; (1994) FASEB J. 8: 217). Enterobacterial LPS consists of three domains, i.e., lipid A, core region and O-specific chain, of which lipid A is structurally the most conserved among different pathogenic bacteria, and represents the toxic principle of LPS(C. A. H. Raetz, (1990) Ann. Rev. Biochem. 59: 129; E. T. Reitschel et al., (1991) Infect. Dis. Clin. North Am. 5: 753; C. Galanos et al., (1985) Eur. J. Biochem. 148: 1). As the toxic effects exerted by LPS are independent of the viability of bacteria and considering the increasing resistance of pathogenic bacteria to antibiotics, the search for alternative treatment strategies for an endotoxin-mediated disorder is of major importance.

Receptors of adaptive and innate immunity share signaling pathways and antigen receptors may have evolved from microbial pattern-recognition receptors (Litman et al., (1999) Annual Review Of Immunology 17: 109-147; Liew et al., (2005) Nature Reviews Immunology 5: 446-458). Cblb expression has also been shown to be up-regulated with monocyte differentiation of HL60 and U937 cell lines (Keane et al., (1995) Oncogene 10: 2367-2377), suggesting its potential importance in the innate immune response.

Thus there exists a need in the art for methods of treating or preventing an endotoxin-mediated disorder.

SUMMARY OF THE INVENTION

The present invention demonstrates a heretofore unknown role for Cblb in regulating innate pattern-recognition receptors. Thus, the effects of Cblb gene deficiency on TLR4 signaling was studied using mouse models of LPS-induced ALI and of polymicrobial sepsis in which acute lung inflammation is dependent on the expression of TLR4 (Alves-Filho et al., (2006) Critical Care Medicine 34: 461-470). Work described herein demonstrates that Cblb is necessary to prevent the inappropriate activation of NFκB in response to LPS and to polymicrobial sepsis.

Thus, the present invention provides methods of treating an endotoxin-mediated disorder or symptom thereof, comprising the step of administering an amount of E3 ubiquitin ligase Cblb, or a biologically active fragment or variant thereof, effective to treat the endotoxin-mediated disorder or symptom thereof.

In various aspects of the invention, the endotoxin-mediated disorder is sepsis.

In an embodiment, the E3 ubiquitin ligase or biologically active fragment or variant thereof is co-administered with a modulator of an immune response.

In still other aspects, the modulator is a stimulator of an immune response.

In another aspect, the stimulator of an immune response is a cytokine.

In a further aspect, the modulator is an inhibitor of an immune response.

In one aspect, the symptom is acute lung injury.

In another aspect, the endotoxin-mediated disorder is selected from the group comprising multi-organ dysfunction syndrome (MODS), kidney failure, and liver failure.

The present invention further provides methods of treating an endotoxin-mediated disorder or symptom thereof, comprising the step of administering an amount of an agent that increases activity of E3 ubiquitin ligase Cblb , or a biologically active fragment or variant thereof, to a level effective to treat an endotoxin-mediated disorder or symptom thereof.

In one aspect, the endotoxin-mediated disorder is sepsis.

In an embodiment, the E3 ubiquitin ligase or biologically active fragment or variant thereof is co-administered with a modulator of an immune response.

In one aspect, the modulator is a stimulator of an immune response.

In a further aspect, the stimulator of an immune response is a cytokine.

In another aspect, the modulator is an inhibitor of an immune response.

In one embodiment, the agent increases expression of E3 ubiquitin ligase Cblb protein.

In another embodiment, the agent increases circulatory half-life of E3 ubiquitin ligase Cblb protein.

In yet another embodiment, the agent increases expression of E3 ubiquitin ligase Cblb mRNA.

In one aspect, the symptom is acute lung injury.

In another aspect, the endotoxin-mediated disorder is selected from the group comprising multi-organ dysfunction syndrome (MODS), kidney failure, and/or liver failure.

Further scope of the applicability of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

DEFINITIONS

Figure 1:
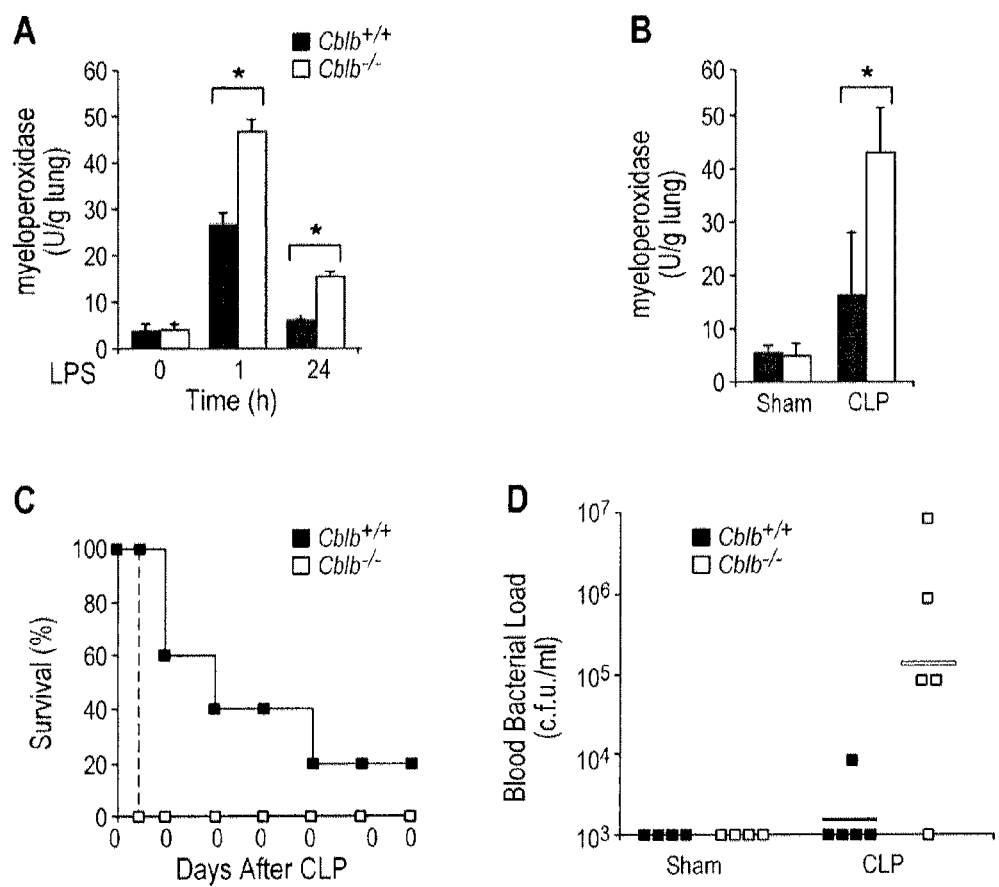
FIG. 1 depicts the genetic deletion of Cblb and the resultant augmentation of sepsis-induced acute lung inflammation and mortality. A) shows a significant increase in lung tissue myeloperoxidase (MPO) activity in wild type mice at 1 hour and 24 hours after injection. B) shows that cecal ligation and puncture (CLP) resulted in increased MPO activity in wild type and Cblb$^{-/-}$ mice. C) shows the survival of CLP-challenged wild-type and Cblb$^{-/-}$ during a 6 day period after surgery. D) depicts that Cblb$^{-/-}$ mice showed a markedly higher number of bacterial colony forming units per ml blood than Cblb$^{+/+}$ mice.

The terms used throughout this specification are defined as follows, unless otherwise limited in specific instances.

As used herein, a Cblb protein is defined as a protein having activities that include, but are not limited to regulating adaptive immunity by setting activation thresholds of mature lymphocytes, induction of T cell tolerance, preventing the inappropriate activation of NF-κB in response to LPS and to polymicrobial sepsis and/or having a functional RING finger domain, which is essential for certain activities of the protein. E3 ubiquitin ligase Cblb protein contemplated for use in the invention include, but are not limited to, GenBank Accession Numbers Q8K4S7, Q3TTA7, Q13191, Q6DFR2, NP_598285, NP_001028410, NP_733762, EDM11080, EDM11079, P22682, and P22681, incorporated herein by reference in their entirety.

A "variant" of Cblb is defined as an amino acid sequence which differs by one or more amino acids from the Cblb sequence. The variant may have "conservative" changes, wherein a substituted amino acid has similar structural or chemical properties. More rarely, a variant may have "nonconservative" changes. Similar variations may also include amino acid deletions or insertions (i.e., additions), or both. A variant may be a peptide as short as four amino acids in length, and as long as a modified full-length Cblb protein. Thus, in one aspect, a variant is greater than five amino acids in length, and less than twenty-five amino acids in length. Of course, these amino acid changes should not significantly interfere with the activity of the compound.

Variants also include fusion proteins, which represent a subset of addition variants. In such cases, the variant may have more amino acids than the naturally-occurring, full-length Cblb peptide. An example, by way of example only, of such a variant is an Fc fusion protein. As contemplated in the invention, the Cblb protein may be fused to either the native Fc or an Fc variant, each of which is discussed hereinafter.

A "biologically active fragment" of a Cblb protein is a fragment containing an amino acid sequence having fewer than all of the amino acids of the full or complete amino acid sequence of Cblb and retaining one or more biological activity associated with the Cblb protein as described herein. Similarly, a "biologically active variant" of a Cblb protein is a variant having an amino acid sequence modification as described herein which retains one or more biological activity associated with the Cblb protein as described herein.

"Ameliorate" as used herein, is defined as: to make better; improve (The American Heritage College Dictionary, 3rd Edition, Houghton Mifflin Company, 2000). The phrase "at risk for developing an endotoxin-mediated disorder" in reference to a subject is herein defined as a subject predisposed to the development of an endotoxin-mediated disorder (e.g., sepsis) by virtue of the subject's medical status, including but not limited to such factors as infection, trauma (e.g., abdominal perforation, such as by a gun shot wound), surgery (e.g., intestinal surgery), burn injury, invasive procedures (e.g., placement of a catheter, etc.) and the like.

The term "vehicle" refers to a molecule that prevents degradation and/or increases half-life, reduces toxicity, reduces immunogenicity, or increases biological activity of a therapeutic protein. Exemplary vehicles include an Fc domain as well as a linear polymer (e.g., polyethylene glycol (PEG), polylysine, dextran, etc.); a branched-chain polymer (See, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); a carbohydrate or oligosaccharide; or any natural or synthetic protein, polypeptide or peptide that binds to a salvage receptor. Vehicles are further described hereinafter. The vehicle is preferably at least one of an Fc domain, polyethylene glycol, a lipid, a cholesterol group, a carbohydrate, and an oligosaccharide. Other suitable vehicles, such as albumin and the like, will be appreciated by those skilled in the art, and are encompassed within the scope of the invention.

Additionally, physiologically acceptable salts of the compounds of this invention are also encompassed herein. By "physiologically acceptable salts" is meant any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate, mesylate, and phosphate.

DETAILED DESCRIPTION OF THE INVENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The present application discloses the unexpected discovery of a heretofore unknown function for Cblb protein (exemplified in SEQ ID NO. 1) as demonstrated using a Cblb gene deficient mouse which is shown to provide a model of hypersensitivity to sepsis. Results herein demonstrate a novel role of Cblb in regulating the TLR4-mediated acute inflammatory response to sepsis. In addition to the previously appreciated functions of Cblb in antigen receptor signaling, the prevention of chronic inflammation and autoimmunity, the present application provides evidence that Cblb has a crucial role in acute inflammation by negatively regulating TLR4 signaling. It is also disclosed that Cblb is necessary to prevent the inappropriate activation of NF-κB in response to LPS and to polymicrobial sepsis. Thus, a protein that evolved to regulate T and B cell receptors also regulates the innate immune receptor TLR4 through polymorphonuclear neutrophils (PMN) and lung endothelial cell activation and be used as a potential therapy to treat an endotoxin-mediated disorder. Accordingly, in one embodiment, the present invention is directed to methods of treating endotoxin-mediated disorders.

Therapeutic uses of Cblb according to the invention include methods of treating conditions associated with endotoxin, such as exposure to gram-negative bacterial endotoxin in circulation, endotoxemia, bacterial and/or endotoxin-related shock and one or more conditions associated therewith, including a systemic inflammatory response, cytokine overstimulation, complement activation, disseminated intravascular coagulation, increased vascular permeability, anemia, thrombocytopenia, leukopenia, pulmonary edema, adult respiratory distress syndrome, renal insufficiency and failure, hypotension, fever, tachycardia, tachypnea, and metabolic acidosis. Thus, not only gram-negative bacterial infection but also its sequelae associated with exposure to gram-negative bacterial endotoxin may be ameliorated through the mediation of the endotoxin-binding or endotoxin-neutralizing activities of TLR4 by Cblb.

In an embodiment, a nucleic acid the encodes a E3 ubiquitin ligase Cblb protein contemplated by the invention can be delivered as an expression construct as described hereinafter. Exemplary proteins contemplated for use in expression constructs are described and referenced herein by GenBank Accession Numbers, and these proteins further include any protein E3 ubiquitin ligase Cblb protein activity. The skilled worker can readily prepare any and all nucleic acid sequences encoding a given protein sequence for incorporation into an expression construct of the invention.

Accordingly, in one embodiment, methods are provided for treating endotoxin-mediated disorders and/or patients at risk for an endotoxin-mediated disorder comprising the step of administering Cblb protein or a biologically active fragment or variant thereof in an amount effective to treat endotoxin-mediated disorders wherein the Cblb protein is administered with an agent having the biological activity of modulating an immune response. Methods provided contemplate the use of any agent that stimulates, promotes or otherwise augments an immune response. In one embodiment, the agent is a cytokine. Exemplary cytokines or hematopoietic factors for such co-administration include IL-1 alpha, IL-1 beta, IL-2, IL-3, IL-5, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-12, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor $2\alpha$, cytokine-induced neutrophil chemotactic factor $2\beta$, $\beta$ endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor $\alpha 1$, glial cell line-derived neutrophic factor receptor $\alpha 2$, growth related protein, growth related protein $\alpha$, growth related protein $\beta$, growth related protein $\gamma$, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor $\alpha$, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor $\alpha$, platelet derived growth factor receptor $\beta$, pre-B cell growth stimulating factor, stem cell factor receptor, TNF, including TNF0, TNF1, TNF2, transforming growth factor $\alpha$, transforming growth factor $\beta$, transforming growth factor $\beta 1$, transforming growth factor $\beta 1.2$, transforming growth factor $\beta 2$, transforming growth factor $\beta 3$, transforming growth factor $\beta 5$, latent transforming growth factor $\beta 1$, transforming growth factor $\beta$ binding protein I, transforming growth factor $\beta$ binding protein II, transforming growth factor $\beta$ binding protein III, urokinase-type plasminogen activator receptor, vascular endothelial growth factor, and chimeric proteins and biologically or immunologically active fragments thereof.

Alternatively, in another embodiment, methods are provided for treating endotoxin-mediated disorders comprising the step of administering Cblb protein or a biologically active fragment or variant thereof in an amount effective to treat endotoxin-mediated disorders wherein the Cblb protein is administered with an agent that inhibits, downregulates or otherwise suppresses an immune response and/or are anti-inflammatory in nature. The anti-inflammatory cytokines are a series of immunoregulatory molecules that control the proinflammatory cytokine response. Cytokines act in concert with specific cytokine inhibitors and soluble cytokine receptors to regulate the human immune response. Their physiologic role in inflammation and pathologic role in systemic inflammatory states are increasingly recognized. Major anti-inflammatory cytokines include interleukin (IL)-1 receptor antagonist, IL-4, IL-6, IL-10, IL-11, and IL-13. Specific cytokine receptors for IL-1, tumor necrosis factor-alpha, and IL-18 also function as proinflammatory cytokine inhibitors (Opal and DePalo, (2000) Chest 117:1162-1172).

In another embodiment, Cblb protein and modulator of an immune response are co-administered with an antibacterial and/or antifungal agent. Known antibacterial agents include antibiotics, which are natural chemical substances of relatively low molecular weight produced by various species of microorganisms, such as bacteria (including *Bacillus* species), actinomycetes (including *Streptomyces*) and fungi, that inhibit growth of or destroy other microorganisms. Substances of similar structure and mode of action may be synthesized chemically, or natural compounds may be modified to produce semi-synthetic antibiotics. These biosynthetic and semi-synthetic derivatives are also effective as antibiotics. The major classes of antibiotics are (1) the $\beta$-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

Known antifungal agents include polyene derivatives, such as amphotericin B (including lipid or liposomal formulations thereof) and the structurally related compounds nystatin and pimaricin; flucytosine (5-fluorocytosine); azole derivatives (including ketoconazole, clotrimazole, miconazole, econazole, butoconazole, oxiconazole, sulconazole, tioconazole, terconazole, fluconazole, itraconazole, voriconazole [Pfizer] and SCH56592 [Schering-Plough]); allylamines-thiocarbamates (including tolnaftate, naftifine and terbinafine); griseofulvin; ciclopirox; haloprogin; echinocandins (including MK-0991 [Merck]); and nikkomycins.

In one embodiment, this invention provides for at least one protein to be attached to at least one vehicle through the N-terminus, C-terminus or a side chain of one of the amino acid residues of the protein. Multiple vehicles may also be used; e.g., an Fc at a terminus and a PEG group at the other terminus or a side chain.

In various embodiments, the Fc component is either a native Fc or an Fc variant. By way of example and without limitation, the Fc component is an Fc region of the human immunoglobulin IgG1 heavy chain or a biologically active fragment, derivative, or dimer thereof, see Ellison, J. W. et al., Nucleic Acids Res. 10:4071-4079 (1982). It is understood, however, that an Fc region for use in the invention may be derived from an IgG, IgA, IgM, IgE or IgD from any species. Native Fc domains are made up of monomeric polypeptides that may be linked into dimeric or multimeric forms by covalent (i.e., disulfide bonds) and/or non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9).

In various aspects, Fc sequence contemplated include those known in the art such as, for example, Fc IgG1 (GenBank Accession No. P01857), Fc IgG2 (GenBank Accession No. P01859), Fc IgG3 (GenBank Accession No. P01860), Fc IgG4 (GenBank Accession No. P01861), Fc IgA1 (GenBank Accession No. P01876), Fc IgA2 (GenBank Accession No. P01877), Fc IgD (GenBank Accession No. P01880), Fc IgM (GenBank Accession No. P01871), and Fc IgE (GenBank Accession No. P01854).

Variants, analogs or derivatives of the Fc portion may be constructed by, for example, making various substitutions of residues or sequences. In one aspect, an Fc variant is incorporated which comprises a molecule or sequence that is humanized from a non-human native Fc. Alternately, an Fc variant comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC), each of which is described in detail in U.S. Patent Application No. 20040087778, the disclosure of which is incorporated by reference in its entirety.

A preferred polymer vehicle is polyethylene glycol (PEG). The PEG group may be of any convenient molecular weight and may be linear or branched. The average molecular weight of the PEG will preferably range from about 2 kiloDalton ("kDa") to about 100 kDa, more preferably from about 5 kDa to about 50 kDa, most preferably from about 5 kDa to about 10 kDa. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group).

Polysaccharide polymers are another type of water soluble polymer which may be used for protein modification. Dextrans are polysaccharide polymers comprised of individual subunits of glucose predominantly linked by α1-6 linkages. The dextran itself is available in many molecular weight ranges, and is readily available in molecular weights from about 1 kDa to about 70 kDa. Dextran is a suitable water-soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kDa to about 20 kDa is preferred when dextran is used as a vehicle in accordance with the present invention.

The compounds used according to the methods of the present invention can be formulated as pharmaceutical compositions, as described in U.S. Patent Publication No. 20060122370, specifically incorporated herein by reference in its entirety. The pharmaceutical composition (or a pharmaceutical salt, derivative or prodrug thereof) may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents [such as ethylenediamine tetraacetic acid (EDTA)]; complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the specific binding agent.

The primary carrier in a pharmaceutical composition may be either aqueous or non-aqueous in nature. For example, a suitable carrier may be water for injection, physiological saline solution or artificial cerebrospinal fluid, possibly supplemented with other materials common in compositions for parenteral administration. Neutral buffered saline or saline mixed with serum albumin are further exemplary carriers. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, binding agent compositions may be prepared for storage by mixing the selected composition having the desired degree of purity with optional formulation agents (Remington's Pharmaceutical Sciences, supra) in the form of a lyophilized cake or an aqueous solution. Further, the binding agent product may be formulated as a lyophilizate using appropriate excipients such as sucrose.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

The pharmaceutical compositions can be selected for parenteral delivery. Alternatively, the compositions may be selected for inhalation or for enteral delivery such as orally, aurally, opthalmically, rectally, or vaginally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired specific binding agent in a pharmaceutically acceptable vehicle. A particularly suitable vehicle for parenteral injection is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

In another embodiment, a pharmaceutical composition may be formulated for inhalation. For example, a binding agent may be formulated as a dry powder for inhalation. Polypeptide inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, binding agent molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the binding agent molecule. Diluents, flavorings, low melting point waxes, vegetable oils, lubricants, suspending agents, tablet disintegrating agents, and binders may also be employed.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

In various embodiments, a Cblb protein or biologically active fragment or variant thereof is administered in 1, 2, 3, 4, 5, 6, 7, 8, 9, 10, 11, 12, 13, 14, 15, 16, 17, 18, 19, 20, 25, 30, 35, 40, 45, 50 or more doses, whether being administered alone or in combination with a second therapeutic as described herein. Thus, in certain embodiments, the Cblb protein or a biologically active fragment or variant thereof and a second therapeutic are co-administered in a weight-toweight ratio of about 0.5:1, about 1:1, about 1:2, about 1:3, about 1:4, about 1:5, about 1:6, about 1:7, about 1:8, about 1:9, about 1:10 or higher, depending on the desired therapeutic benefit and other considerations regarding the recipient understood by a practicing clinician.

For any compound, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

The invention is illustrated by the following examples, which are not intended to be limiting in any way.

EXAMPLES

Example 1

Genetic Deletion of Cblb Augments Lung Inflammation

All mice were bred and maintained under specific pathogen-free conditions at the University of Illinois animal facility. $Cblb^{-/-}$ mice, as described (Bachmaier et al., (2000) Nature 403: 211-216), were backcrossed into a BALB/c background for 9 generations. The $Cblb^{+/+}$ and $Cblb^{-/-}$ mice used for all experiments were maintained in F9. For all experiments, 7-14 wk old mice were used. Cbl proteins are expressed in normal lungs and in polymorphonuclear neutrophils (PMNs), both in mice and humans (Naccache et al., (1997) Journal Of Leukocyte Biology 62: 901-910), but nothing is known about the function of Cblb in ALI (Richards, (2005) Clinical Microbiology And Infection 11: 18-22). LPS, given intraperitoneally, resulted in a significant increase in lung tissue myeloperoxidase (MPO) activity, a quantitative measure of PMN sequestration, in wild type mice at 1 h and 24 h after injection (FIG. 1A). Lungs were perfused with PBS to remove all blood. Lungs were weighed and frozen and stored at −80° C. for no more than 1 week before MPO assay was performed. MPO activity was measured as previously described (Hickey et al., (2002) Faseb Journal 16). Strikingly, Cblb gene deficient ($Cblb^{-/-}$) mice showed significantly greater MPO activity when compared to wild type ($Cblb^{+/+}$) controls (FIG. 1A). In both $Cblb^{+/+}$ and $Cblb^{-/-}$ mice, lung sections showed sequestration of inflammatory cells in capillary and extra-capillary spaces, but not in alveoli at 6 h after LPS challenge. Mice received a single dose (0.5 mg/kg) of LPS (*E. coli* 0111:B4, InvivoGen) intraperitoneally. Inflammatory cells were absent in lungs of untreated mice of either genotype. There was no apparent difference in the phenotype of inflammatory cells between the genotypes. Leder (esterase) staining showed that in $Cblb^{+/+}$ and $Cblb^{-/-}$ mice the inflammatory cells were primarily PMNs. These data indicated that the significantly increased MPO activity in lungs of $Cblb^{-/-}$ mice was due to augmented sequestration of PMNs.

To evaluate the pathobiological relevance of these findings cecal ligation and puncture (CLP) was used. Polymicrobial sepsis was induced by cecal ligation and puncture (CLP) using a 16-gauge needle. In sham controls, only laparotomy was performed. CLP causes lethal peritonitis and sepsis due to a polymicrobial infection that is accompanied by ALI. In this model, PMN migration into lungs is dependent on TLR4 expression (Alves-Filho et al., (2006) Critical Care Medicine 34: 461-470), which allows one to address the role of Cblb in regulating TLR4 signaling. CLP resulted in increased MPO activity (FIG. 1B) in wild type and $Cblb^{-/-}$ mice. CLP-challenged $Cblb^{-/-}$ mice, however, showed a significant increase in PMN accumulation when compared to wild-type mice (FIG. 1B). Whereas all CLP-challenged wild-type mice survived the first 12 h period after surgery, all CLP-challenged $Cblb^{-/-}$ mice died within this time period (FIG. 1C). All sham treated mice survived (FIG. 1C). For survival studies, mice were monitored twice daily for 6 days. Thus, Cblb negatively regulates TLR4 signaling in polymicrobial sepsis. The loss of Cblb expression worsens acute lung inflammation and survival after polymicrobial sepsis. TLR4-deficiency in mice undergoing lethal CLP leads to low bacteremia and high survival rate (Alves-Filho et al., (2006) Critical Care Medicine 34: 461-470). Since Cblb -gene deficient mice die within 12 hours of lethal CLP, the mice were sacrificed 4 h after the procedure to determine the extent of TLR4-dependent bacteremia. $Cblb^{-/-}$ mice showed a markedly higher number of bacterial colony forming units per ml blood than $Cblb^{+/+}$ mice (FIG. 1D). One hundred microliters of blood was collected by cardiac puncture 4 h after CLP. The blood volume was brought up to 0.5 ml with distilled water and dilutions (1:2, 1:100, 1:1,000) were prepared and plated on LB agar plates. Plates were incubation for 24 h and bacterial colonies were counted and the number of colony forming units per ml blood was calculated.

Example 2

Figure 2:
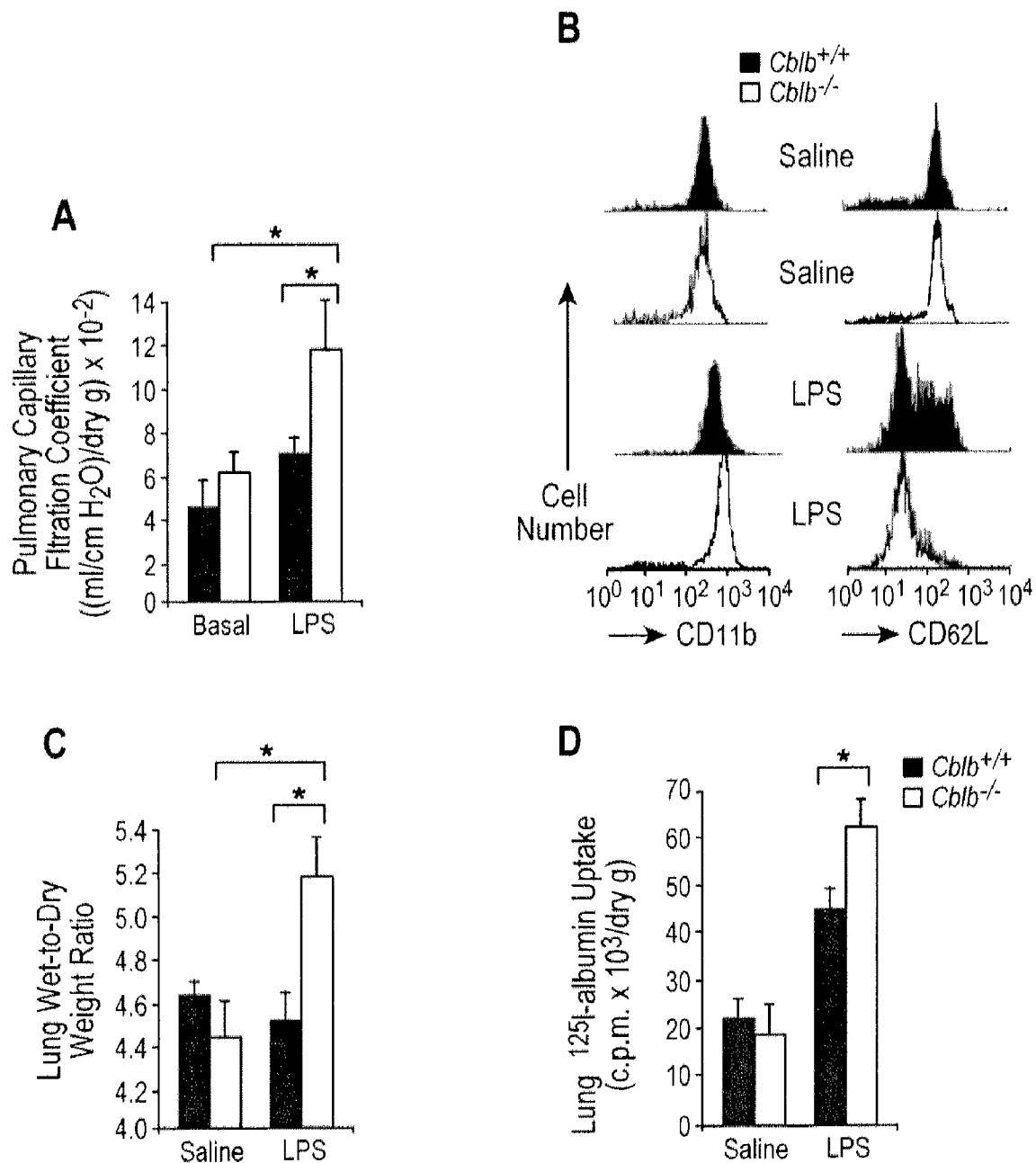
FIG. 2 depicts Cblb regulation of lung microvascular endothelial integrity and polymorphonuclear neutrophil (PMN) activation in response to LPS challenge. A) shows that stimulation with LPS significantly increased $K_{f,c}$ of lungs from Cblb$^{-/-}$ mice, whereas $K_{f,c}$ was not significantly different from basal level in lungs from Cblb$^{+/+}$ controls. B) shows that in Cblb$^{-/-}$ mice, there was more pronounced upregulation of CD11b and more rapid shedding of CD62L compared to Cblb$^{+/+}$ control mice. C) shows that pulmonary edema was observed in mice lacking Cblb but not in their wild type controls after LPS challenge. D) shows the uptake of $^{125}$I-albumin in Cblb$^{-/-}$ and Cblb$^{+/+}$ mice after LPS challenge.

Loss of Cblb Leads to Activation of Lung Vascular Endothelium Following LPS Challenge Activation of the lung endothelium via TLR4 signaling after systemic administration of LPS is a prerequisite for PMN sequestration in lungs (Andonegui et al., (2003) Journal Of Clinical Investigation 111: 1011-1020). To determine whether loss of Cblb leads to activation of the lung vascular endothelium in response to LPS, the isolated-perfused lung model was used in which the pulmonary microvessel filtration coefficient ($K_{f,c}$), a quantitative measure of vascular endothelial permeability, is used as a functional measure of endothelial activation. $K_{f,c}$ measurements on isolated lung preparations were performed as described (Tiruppathi et al., (2002) Circulation Research 91: 70-76). Prior to $K_{f,c}$ measurements, lungs were perfused for 20 min with modified Krebs-Henseleit solution with or without LPS (100 ng/ml). To measure pulmonary vascular uptake of albumin, mice received a single dose (5 mg/kg) of LPS (*E. coli* 0111:B4) intraperitoneally. At 2 h, mice were injected with 1 µCi of $^{125}$I-labeled albumin, and killed 1 h after injection of the albumin tracer (Zhou et al., (1998) Journal Of Clinical Investigation 101: 2427-2437). Stimulation with LPS significantly increased $K_{f,c}$ of lungs from Cblb$^{-/-}$ mice, whereas $K_{f,c}$ was not significantly different from basal level in lungs from Cblb$^{+/+}$ controls (FIG. 2A). Importantly, basal $K_{f,c}$ was similar in both strains (FIG. 2A). These results show that Cblb is a negative regulator of TLR4 signaling in the lung endothelium, thus facilitating the maintenance of lung endothelial barrier integrity after LPS challenge.

To determine whether loss of Cblb has an effect on PMN activation, CD62L (L-selectin) shedding and CD11b upregulation was measured (Andonegui et al., (2003) Journal Of Clinical Investigation 111: 1011-1020). Mice were challenged intraperitoneally with LPS, and after 1 h, CD62L and CD11b expression on the cell surface of peripheral blood PMNs was determined by flow cytometry. In Cblb$^{-/-}$ mice, there was more pronounced upregulation of CD11b and more rapid shedding of CD62L compared to Cblb$^{+/+}$ control mice (FIG. 2B). Basal expression of CD11b and CD62L on the cell surface was comparable between genotypes (FIG. 2B). CD62L shedding, while dependent on TLR4 expression on leukocytes, is independent of the presence of TLR4 in endothelial cells (Andonegui et al., (2003) Journal Of Clinical Investigation 111: 1011-1020), suggesting that the enhanced effect of LPS on CD62L shedding in Cblb$^{-/-}$ mice was due to lack of negative regulation of TLR4 signaling in leukocytes in these mice.

Dysregulation of TLR4 signaling in lung endothelium and PMNs may lead to pulmonary edema, an important component of the acute respiratory distress syndrome, the most severe form of ALI (Ware and Matthay (2000) New England Journal Of Medicine 342: 1334-1349). Pulmonary edema, measured as a significant increase in the wet-to-dry lung weight ratio, was observed in mice lacking Cblb but not in their wild type controls after LPS challenge (FIG. 2C). Next the uptake of $^{125}$I-albumin was analyzed as an in vivo indicator of pulmonary microvessel albumin leakage. In Cblb$^{-/-}$ mice pulmonary $^{125}$I-albumin leakage was significantly greater than in Cblb$^{+/+}$ mice after LPS challenge. Basal lung $^{125}$I-albumin leakage was comparable between the genotypes (FIG. 2D).

Example 3

Pro-Inflammatory Phenotype of Cblb Gene-Deficient Cells

Figure 3:
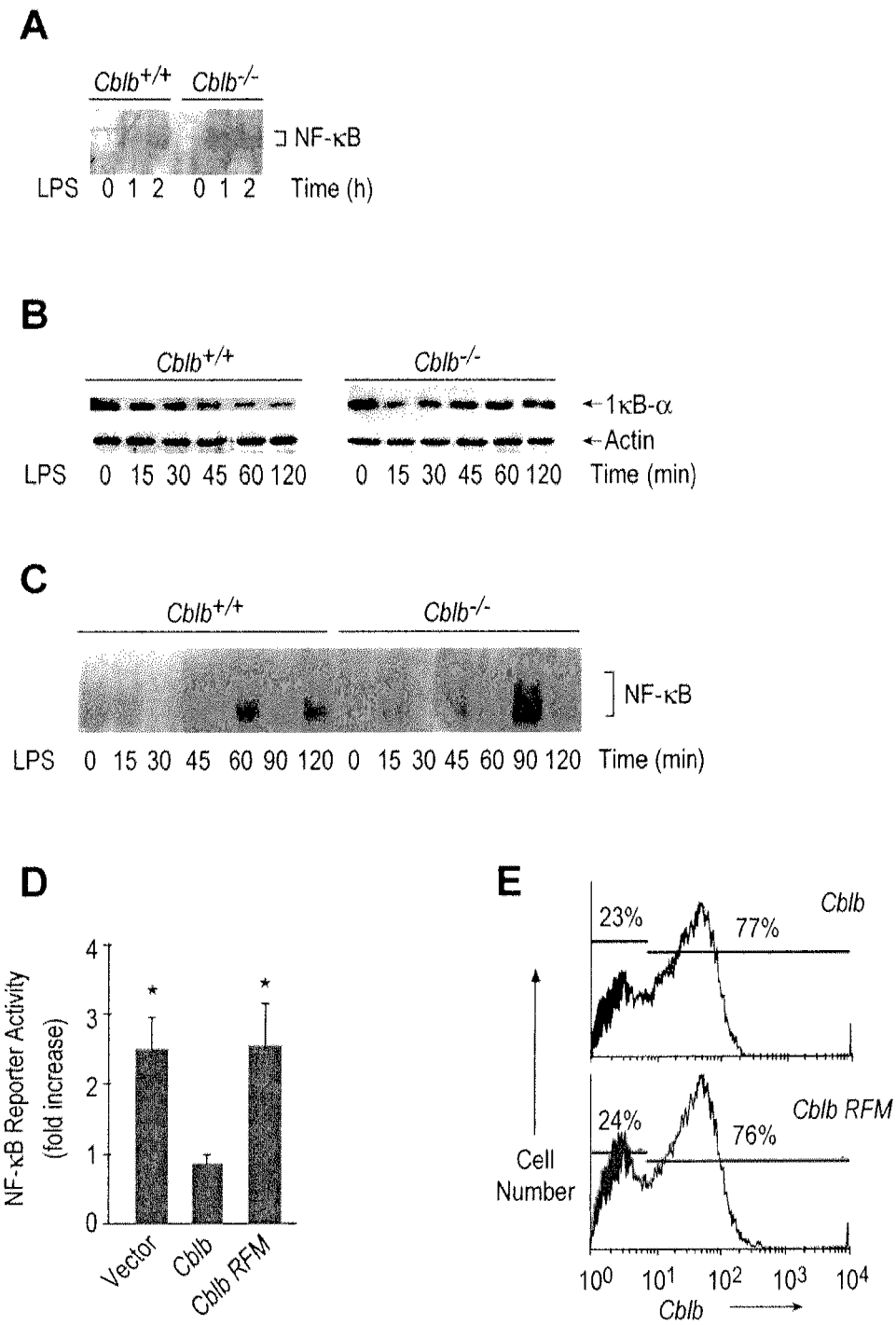
FIG. 3 depicts Cblb regulation of NF-kB activation following LPS challenge. A) shows the assessment of the presence of NF-κB proteins in nuclear extracts from lung tissue of Cblb$^{-/-}$ and Cblb$^{+/+}$ mice before and after LPS challenge. B) shows the IκB-α protein levels of Cblb$^{-/-}$ and Cblb$^{+/+}$ mice after stimulation with LPS over a 2 hour observation period. C) shows the in nuclear translocation of NF-κB proteins in Cblb$^{-/-}$ and Cblb$^{+/+}$ mouse splenocytes. D) shows results of a study designed to address whether Cblb inhibits NF-κB activation upon LPS stimulation. E) shows that transfection of monocytes with Cblb or Cblb RFM constructs led to comparable expression of the proteins.

LPS signaling activates the transcription factor nuclear factor-κB (NF-κB) involved in lung vascular permeability (Ankermann et al., (2005) Critical Care Medicine 33: 1384-1391; Matsuda et al., (2005) Molecular Pharmacology 67: 1018-1025). Therefore, the presence of NF-κB proteins was assessed in nuclear extracts from lung tissue before and after LPS challenge. There were no NF-κB proteins detectable in nuclear extracts of lungs from unchallenged mice of either genotype (FIG. 3A). After LPS challenge, however, rapid and augmented NF-κB translocation to nuclei in lungs from Cblb$^{-/-}$ mice compared to Cblb$^{+/+}$ controls was observed (FIG. 3A).

To test whether Cblb negatively regulates NF-κB activation upon stimulation with LPS, PMNs were stimulated with LPS and protein levels of the inhibitor of NF-κB (IκB) α were determined. Stimulation of PMNs with LPS rapidly activates signaling via the MyD88-dependent pathway leading to degradation of IκB (Barton and Medzhitov, (2003) Science 300: 1524-1525). In PMNs from Cblb$^{+/+}$ mice, IκB-α protein levels decreased continuously after stimulation with LPS over the 2 h observation period (FIG. 3B). In PMNs from Cblb$^{-/-}$ mice, IκB-α levels decreased more rapidly compared to wild type controls, and IκB-α protein level was higher 60 min after LPS challenge than 45 min after LPS (FIG. 3B). Degradation of IκB frees NF-κB to translocate to the nucleus and bind target genes. Nuclear extracts were prepared from lung specimens after in vivo stimulation of mice with LPS (0.5 mg/kg), or from splenocytes, suspended in PBS plus 1% BSA, stimulated with LPS (2 µg/ml), at 37° C. NF-κB oligonucleotide containing the NF-κB consensus sequence 5'-AGTTGAGGGGACTTTCCCAGGC-3' (SEQ ID NO: 2) was used and EMSA was performed according to standard methods. In splenocytes from Cblb$^{+/+}$ mice, stimulation with LPS induced marked nuclear translocation of NF-κB proteins that exhibited an oscillatory phenotype (FIG. 3C). An oscillatory phenotype was also observed in Cblb$^{-/-}$ cells. Translocation of NF-κB proteins occurred, however, more rapidly in cells from Cblb$^{-/-}$ mice, with a significant increase in nuclear NF-κB proteins first seen 15 min after stimulation with LPS compared to 45 min in cells from Cblb$^{+/+}$ mice. Moreover, NF-κB protein nuclear translocation was greater in cells from Cblb$^{-/-}$ mice (FIG. 3C).

IκB-α is an important target gene of NF-κB (Sun et al., (1993) Science 259: 1912-1915; Hoffmann et al., (2002) Science 298: 1241-1245). The finding that IκB-α protein level increased at 1 h after stimulation with LPS in Cblb$^{-/-}$ cells, and not in Cblb$^{+/+}$ cells, is consistent with the accelerated and augmented activation of NF-κB seen in the absence of Cblb. In the LPS-induced lung injury model, neutralization of MIP-1α was shown to attenuate PMN infiltration into inflammatory sites of mice (Standiford et al., (1995) Journal Of Immunology 155: 1515-1524), reduce pulmonary vascular permeability in rats (Shanley et al., (1995) Journal Of Immunology 154: 4793-4802), and reduce the migration of PMNs isolated from inflammatory exudates in response to a MIP-1α chemotactic gradient (Gao et al., (1997) Journal Of Experimental Medicine 185: 1959-1968). TNF-α also triggered mononuclear cell and PMN infiltration in lungs, liver, and kidneys (Neumann et al., (1996) Journal Of Immunology 156: 1587-1593). The disclosed findings showing enhanced production of MIP-1α and TNF-α in sera of LPS- or CLP-challenged mice and tissue culture supernatants of LPS-exposed splenocytes are consistent with an important role of MIP-1α and TNF-α in inducing lung inflammation in Cblb$^{-/-}$ mice. The clinical relevance of these findings is underscored by the fact that a drug used to treat sepsis, recombinant human activated protein C, at supra-pharmacological concentration, inhibited NF-κB activity and release of MIP-1α in mononuclear cells isolated from patients with severe sepsis (Brueckmann et al., (2004) Inflammation Research 53: 528-533). Bacteremia in CLP is TLR4-dependent in that TLR4 deficient mice showed low bacteremia (Alves-Filho et al., (2006) Critical Care Medicine 34: 461-470). Therefore, in mice in which TLR4 signaling is enhanced, as is the case in Cblb$^{-/-}$ mice, one would expect increased bacteremia, consistent with the disclosed observation.

To address directly the question whether Cblb inhibits NF-κB activation upon LPS stimulation, a mouse macrophage cell line that constitutively expresses a NF-κB reporter construct was utilized. In these cells Cblb or Cblb with a point mutation that abrogates E3 ubiquitin ligase function (Cblb RFM) was overexpressed (Ettenberg et al., (2001) Journal of Biological Chemistry 276: 27677-27684; Ettenberg et al., (1999) Oncogene 18; 1855-1866). Cblb overexpression reduced LPS-induced NF-κB reporter activity to the level seen in non-transfected unstimulated controls (FIG. 3D). Conversely, overexpression of the Cblb RFM failed to suppress LPS-induced NF-κB activation, similar to Vector-transfected control (FIG. 3D). Transfection of monocytes with Cblb or Cblb RFM constructs led to comparable expression of the proteins (FIG. 3E). These data show that Cblb suppresses NF-κB activation in response to LPS in an E3 ubiquitin ligase-dependent manner.

Example 4

Cytokine and Chemokine Measurements

Figure 4A:
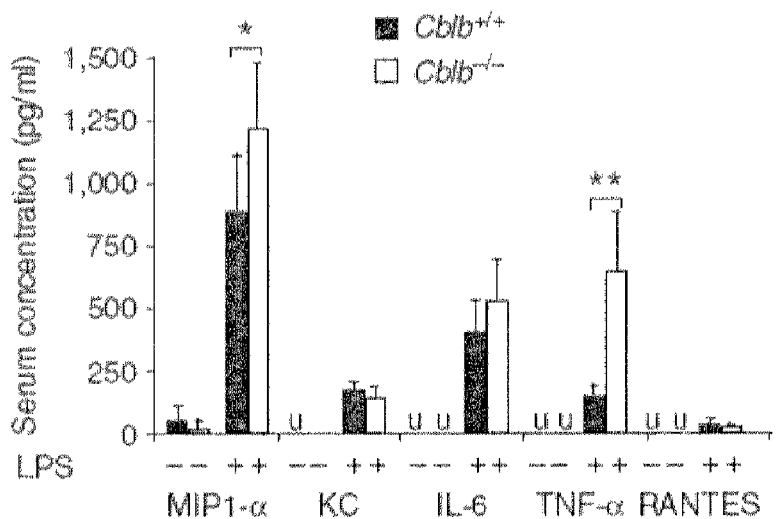
FIG. 4 demonstrates that deletion of Cblb augments sepsis-induced cytokine and chemokine production. A) shows serum levels of TNF-α, MIP-1α, KC, RANTES and IL-6 in Cblb$^{-/-}$ and Cblb$^{+/+}$ mice. B) shows concentrations after CLP of these cytokines and chemokines in sera from Cblb$^{-/-}$ mice compared to Cblb$^{+/+}$ controls. C) shows supernatant concentrations of the cytokines and chemokines. D) shows that genetic deletion of Cblb had no appreciable effect on TLR3-dependent cytokine and chemokine production as induced by polyinosine-polycytidylic acid. E) shows that administration of Cblb plasmid led to expression of Cblb protein in lungs of Cblb$^{-/-}$ mice. F) shows that challenge of Cblb$^{-/-}$ mice with LPS 46 hours after Cblb plasmid administration for 2 hours resulted in a reduction in lung inflammation as compared to Vector plasmid treated Cblb–/– controls, as assessed by lung tissue MPO activity. G) shows that the Cblb plasmid treated Cblb$^{-/-}$ mice had significantly reduced serum cytokine and chemokine levels after LPS challenge compared to Vector plasmid treated Cblb$^{-/-}$ controls.
Figure 4B:
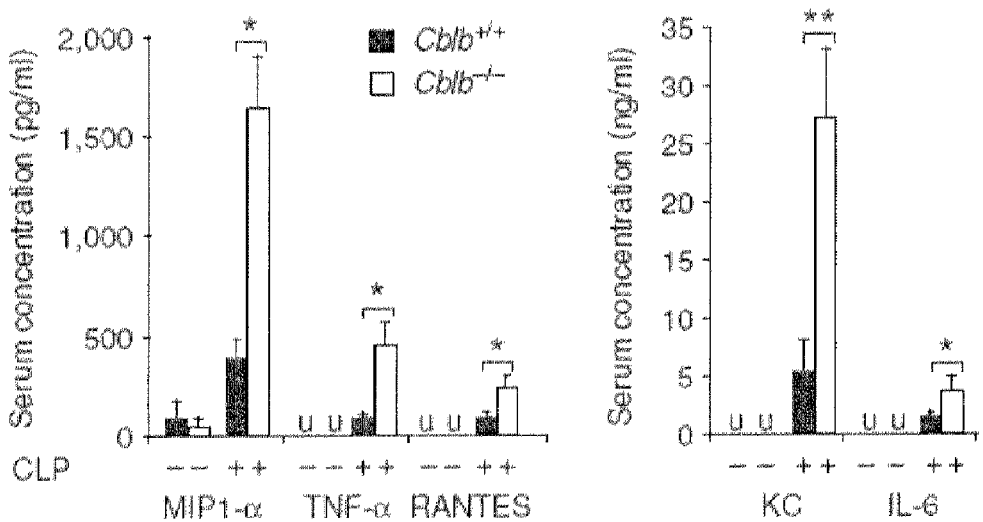
Figure 4C:
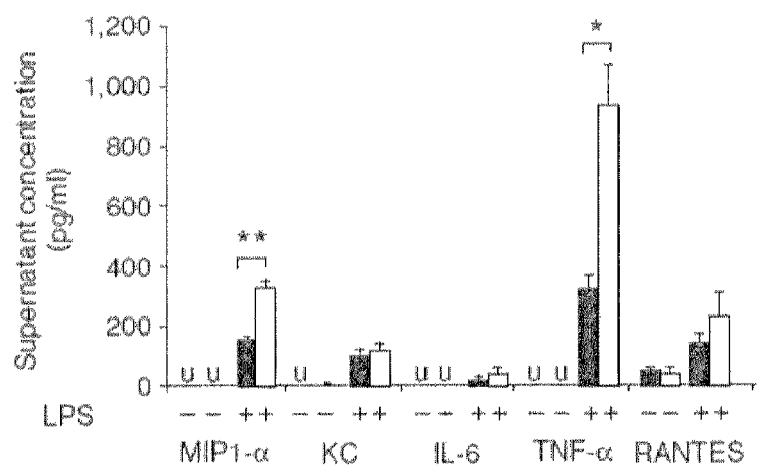
Figure 4D:
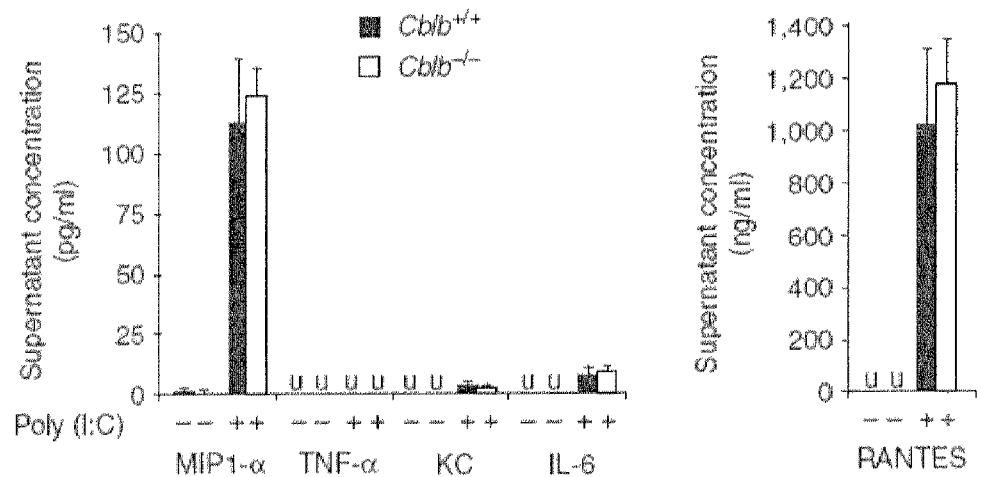

To explore the functional consequences of the accelerated and augmented nuclear translocation of NF-κB proteins, cytokines and chemokines encoded by target genes of NF-κB proteins were measured (Grove and Plumb, (1993) Molecular And Cellular Biology 13: 5276-5289; Karin and Greten, (2005) Nature Reviews Immunology 5: 749-759), and implicated in PMN sequestration in lungs, namely MIP-1α, KC, IL-6, TNF-α, and RANTES. To determine cytokine and chemokine levels, splenocytes from naïve mice were placed into 12-well tissue culture plates ($1.5 \times 10^6$ cells/well) in IDMD plus 10% FBS. Cells were stimulated for 2 h in a $CO_2$ incubator at 37° C. with LPS (2 µg/ml) or polyinosine-polycytidylic acid (25 µg/ml), or IDMD plus 10% FBS alone. Tissue culture supernatants as well as sera from Cblb$^{+/+}$ and Cblb$^{-/-}$ mice injected with LPS (0.5 mg/kg) or saline, were analyzed for the presence of IL-6 and TNF-α, MIP-1α, KC, and RANTES using the Bio-Plex Multiplex Cytokine Assay (Bio-Rad). At 2 h after intraperitoneal administration of LPS, serum level of TNF-α were drastically higher in Cblb$^{-/-}$ mice than Cblb$^{+/+}$ controls (FIG. 4A). MIP-1α levels were significantly greater in Cblb$^{-/-}$ mice than in Cblb$^{+/+}$ controls (FIG. 4A). KC, RANTES, and IL-6 serum levels were comparable in both strains (FIG. 4A). Inhibition of NF-κB activation prevents acute lung injury in mice with CLP-induced sepsis (Matsuda et al., (2005) Molecular Pharmacology 67: 1018-1025). Thus, the serum levels of NF-κB activation-dependent MIP-1α, KC, IL-6, TNF-α, and RANTES after CLP were determined. Concentrations of these cytokines and chemokines were significantly greater in sera from Cblb$^{-/-}$ mice compared to Cblb$^{+/+}$ controls (FIG. 4B). In vitro, after stimulation with LPS for 2 h, TNF-α and MIP-1α concentrations were significantly increased in tissue culture supernatants of splenocytes from Cblb$^{-/-}$ mice compared to splenocytes from Cblb$^{+/+}$ controls (FIG. 4C). KC, RANTES, and IL-6 concentration were comparable in these culture supernatants (FIG. 4C). Production of MIP-1α, KC, IL-6, TNF-α, and RANTES, both in vivo and in vitro, depended on the challenge with LPS or CLP. Genetic deletion of Cblb, on the other hand, had no appreciable effect on TLR3-dependent cytokine and chemokine production as induced by the TLR3-specific agonist polyinosine-polycytidylic acid (FIG. 4D).

Figure 4E:
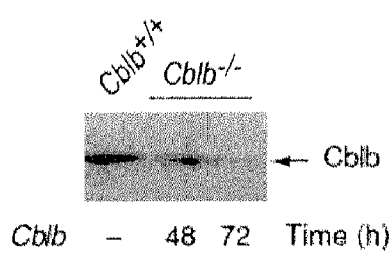
Figure 4F:
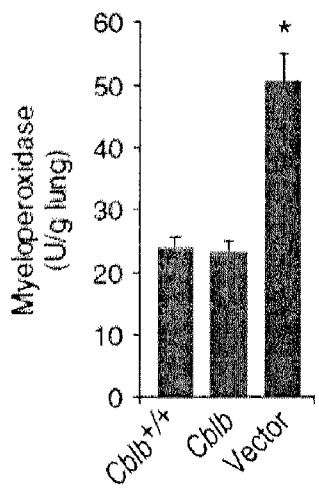
Figure 4G:
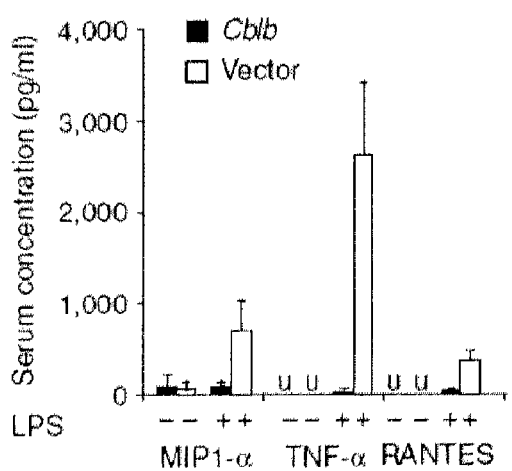
Figure 4G:
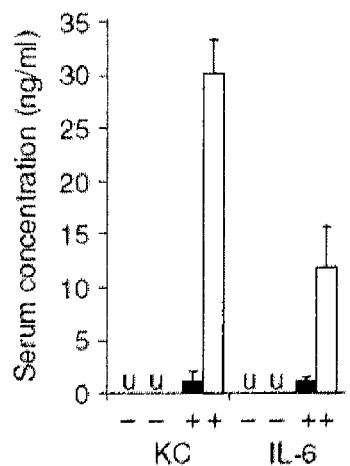

To address whether Cblb is essential for the control of acute lung inflammation induced by a TLR4 agonist, an in vivo rescue experiment was performed. A Cblb plasmid was administered using the liposome method (Zhou et al., (1998) Journal Of Clinical Investigation 101: 2427-2437). Liposomes were prepared as described (Zhou et al., (1998) Journal Of Clinical Investigation 101: 2427-2437). The complex consisting of the Cblb -expression plasmid, or the empty vector (8.5 pmol per mouse), and liposomes were combined at the ratio of 0.34 pmol of DNA to 8 nmol of liposomes. Plasmids and liposomes were injected into the retro-orbital venous plexus. Administration of Cblb plasmid led to expression of Cblb protein in lungs of Cblb$^{-/-}$ mice. At 48 h after plasmid administration Cblb protein expression was comparable to the expression of Cblb in lungs of wild type controls (FIG. 4E). Cblb protein was absent in Cblb$^{-/-}$ mice that received liposomes plus control plasmid. Challenge of Cblb$^{-/-}$ mice with LPS 46 h after Cblb plasmid administration for 2 h resulted in a significant reduction in lung inflammation as compared to Vector plasmid treated Cblb$^{-/-}$ controls (FIG. 4F). Lung tissue MPO activity was comparable to Cblb controls (FIG. 4F). The Cblb plasmid treated Cblb$^{-/-}$ mice had significantly reduced serum cytokine and chemokine levels after LPS challenge compared to Vector plasmid treated Cblb$^{-/-}$ controls (FIG. 4G). These data show that Cblb is essential for regulating acute lung inflammation induced by a TLR4 agonist.

Example 5

Impaired Trafficking of Signaling Proteins in Cblb-Deficient Cells

Figure 5:
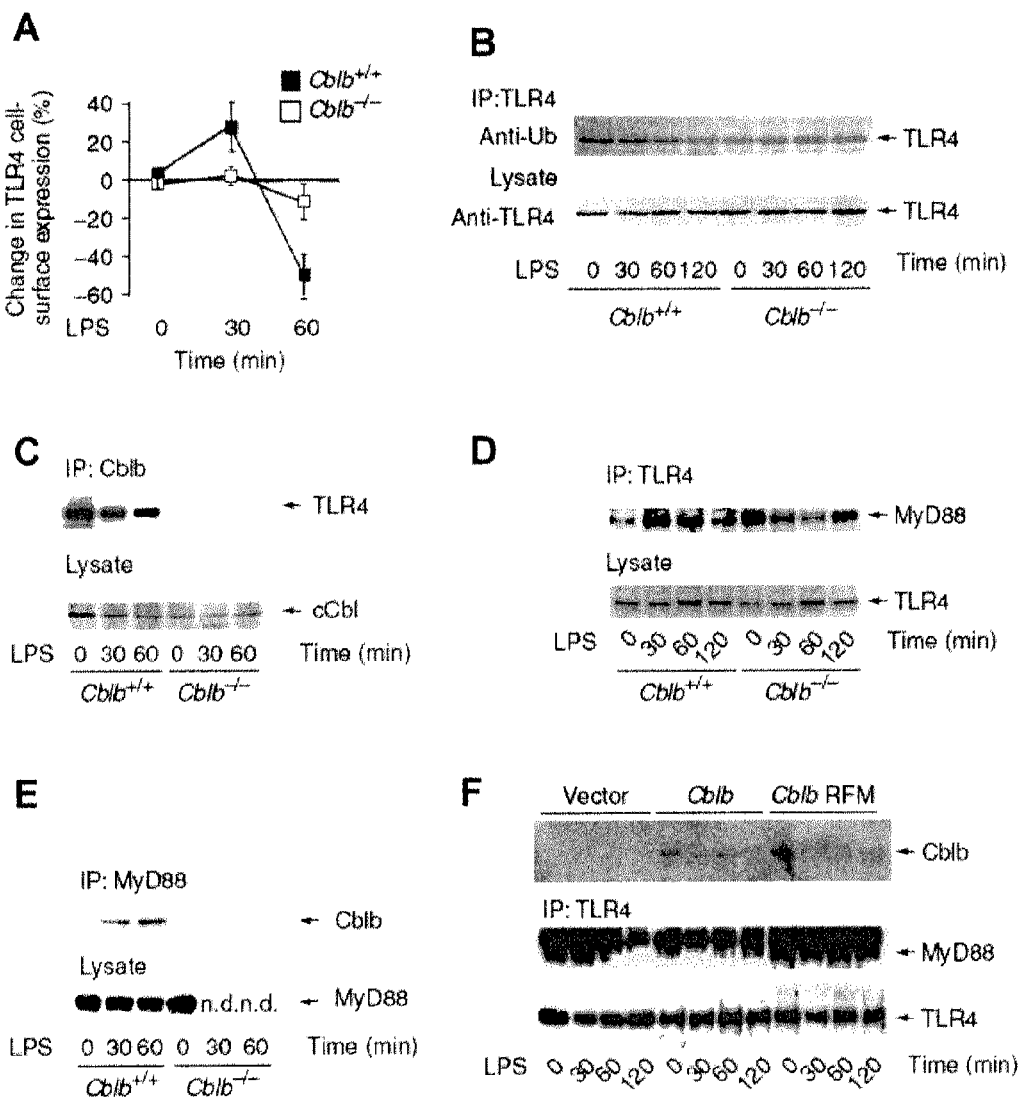
FIG. 5 depicts Cblb regulation of the association between TLR4 and MyD88 after LPS stimulation. A) shows the change in TLR4 cell surface expression after LPS challenge in Cblb$^{-/-}$ and Cblb$^{+/+}$ mice. B) shows the relative ubiquitination in and Cblb$^{-/-}$ and Cblb$^{+/+}$ mice of TLR4 after stimulation with LPS. C) the association of Cblb with TLR4 in Cblb$^{-/-}$ and Cblb$^{+/+}$ mice upon stimulation with LPS. D) shows the effect of Cblb deficiency on the association of TLR4 with MyD88. E) shows the association of MyD88 and Cblb . F) shows that Cblb prevented the assoxciation between TLR4 and MtD88.

Given the role of Cblb proteins in the control of antigen and growth factor receptors (Naramura et al., (2002) Nature Immunology 3: 1192-1199; Soubeyran et al., (2002) Nature 416: 183-187), it is possible that Cblb regulates the cell surface expression of TLR4. Thus, cell surface expression of TLR4 on peripheral blood PMNs in vitro was analyzed. To study trafficking, cells were suspended in PBS containing 1% BSA, and stimulated with LPS (2 µg/ml) at 37° C. Cells were lysed in ice-cold buffer (100 mM Tris-HCL (ph 7.5), 5 mM EDTA, 50 mM NaCl, 5 mM EGTA, 1 mM $Na_3VO_4$, 50 mM NaF, 0.25% Na-deoxycholic acid, 0.1% SDS, 1% Triton X100, 10 µg/ml protease inhibitors). The antibodies used to immunoprecipitate TLR4 were from BD Pharmigen (558293), and, for immunoblotting, from Cell Signaling (2246). The antibodies to detect or immunoprecipitate: MyD88 (sc-8197), cCbl (sc-170), Cblb (sc-1435), Cblb (sc-8006 for IP and flow cytometry), actin (sc-1616), IκB-α (sc-371) were from Santa Cruz. The anti-human MyD88 Ab (14-6223) was from eBioscience, and anti-Ubiquitin Ab (P4D1) was from Cell Signaling. Peripheral blood leukocytes, resuspended in PBS plus 1% BSA and stimulated with LPS (2 µg/ml) at 37° C., were stained in triplicates with anti-TLR4 antibody (BD Pharmigen, 558293), and analyzed on a LSR flow cytometer (Becton Dickinson). The percentage of receptor up- or down-regulation was determined based on the mean fluorescence intensity (MFI) of receptor expression on stimulated versus unstimulated cells with the following formula: percentage change=((MFI stimulated at time t−MFI unstimulated at time t)/MFI unstimulated at time 0)×100. Unstimulated PMNs from Cblb$^{-/-}$ and Cblb$^{+/+}$ mice showed similar expression levels of TLR4 on the cell surface (not shown). After LPS challenge, an initial upregulation of TLR4 was observed, which was more pronounced in PMNs from Cblb$^{+/+}$ mice, and subsequent downregulation of the receptor in PMNs from both strains (FIG. 5A). However, at 1 h after stimulation with LPS, TLR4 downregulation was much more pronounced in PMNs from Cblb$^{+/+}$ mice compared to PMNs from Cblb$^{-/-}$ mice (FIG. 5A). Thus, in response to LPS, Cblb in PMNs is necessary for the appropriate TLR4 surface expression and the subsequent downregulation of TLR4 from the cell surface.

Ubiquitination, inducible and reversible, is an important mechanism controlling intracellular trafficking of proteins (Haglund and Dikic, (2005) EMBO Journal 24: 3353-3359). Therefore, whether the absence of Cblb alters the ubiquitination of TLR4 was determined. In freshly isolated splenocytes from Cblb$^{+/+}$ mice, ubiquitination of TLR4 decreased after stimulation with LPS (FIG. 5B). In contrast, TLR4 was markedly less ubiquitinated in cells from Cblb$^{-/-}$ mice, and ubiquitination did not change with LPS stimulation (FIG. 5B). The decrease in ubiquitinated TLR4 protein in wild type cells was not due to proteasomal degradation since the cells were stimulated in the presence of the proteasomal inhibitor MG-132. In addition, total TLR4 protein levels remained steady over the stimulation period (FIG. 5B). In freshly isolated splenocytes from naïve wild type animals, Cblb was associated with TLR4 (FIG. 5C). There was less association of Cblb with TLR4 upon stimulation with LPS (FIG. 5C), correlating with the decrease in ubiquitination of TLR4 protein observed after LPS stimulation (FIG. 5B).

Next, the effect of Cblb deficiency on the association of TLR4 with MyD88 was studied. In freshly isolated splenocytes from Cblb$^{-/-}$ mice, an augmented association of MyD88 and TLR4 under basal conditions was noted and no noticeable change in association of TLR4 and MyD88 upon stimulation with LPS (FIG. 5D). In wild type splenocytes, the expected pattern of association between MyD88 and TLR4 was seen, i.e., a transient increase of association between TLR4 and MyD88 upon stimulation with LPS (FIG. 5D), and MyD88 and Cblb were only associated after LPS stimulation (FIG. 5E).

To test directly the possibility that Cblb prevents the association between MyD88 and TLR4, Cblb and Cblb RFM were overexpressed in HEK293 cells that stably expressed TLR4, CD14, and MD2, and are thus responsive to LPS. Immortalized mouse bone marrow derived macrophages (BMDM) were generated that stably express an inducible NF-κB driven luciferase reporter construct from HLL transgenic mice (Blackwell et al., (1999) American Journal Of Respiratory And Critical Care Medicine 159: A499-A499), HLL-BMDM, using a described method (Bosco et al., (2000) Journal Of Immunology 164: 3283-3291). RING finger mutant (Cblb RFM), or Cblb expression plasmids (Ettenberg et al., (2001) Journal Of Biological Chemistry 276: 27677-27684; Ettenberg et al., (1999) Oncogene 18: 1855-1866) or Vector only plasmid were transfected in HLL-BMDM by electroporation (Melkonyan et al., (1996) Nucleic Acids Research 24: 4356-4357). To transfect Cblb RFM and Cblb expression plasmids into HEK293 cells that constitutively express the mouse TLR4, MD2, and CD14 genes (Invivigen, 293-mtlr4md2cd14), using a Superfect (Qiagen). At 72 h after transfection of plasmids, cells were stimulated with LPS (1 μg/ml). Cblb , but not Cblb RFM, prevented the association between TLR4 and MyD88 (FIG. 5F). Importantly, overexpression of Cblb did not induce the degradation of TLR4 (FIG. 5F). Thus, the findings indicate that Cblb regulates the cell surface expression of TLR4 in response to LPS and that Cblb regulates the association of MyD88 and TLR4, thereby negatively regulating TLR4 signaling through the MyD88-dependent pathway.

Evidence herein shows that Cblb controls TLR4 signaling to prevent hyperactivation of NF-κB by two distinct mechanisms. First, Cblb deficient cells fail to downregulate TLR4 rapidly after initiation of TLR4 stimulation. Second, Cblb deficient cells fail to regulate the association of TLR4 and MyD88. The finding that Cblb overexpression prevents the association of TLR4 and MyD88 validated the latter mechanism. This requires E3 ubiquitin ligase function since overexpression of Cblb RFM did not prevent the association of TLR4 and MyD88. Genetic deletion of Cblb had no appreciable effect on TLR3-dependent cytokine and chemokine production, indicating that Cblb controls signaling relayed by MyD88, but not signaling relayed by the TLR3-specific adaptor TRIF (Yamamoto et al., (2003) Science 301: 640-643).

The references cited herein throughout, to the extent that they provide exemplary details supplementary to those set forth herein, are all specifically incorporated herein by reference.

What is claimed is:

1. A method of treating an endotoxin-mediated disorder or symptom thereof, comprising the step of administering an amount of E3 ubiquitin ligase Cblb effective to treat the endotoxin-mediated disorder or symptom thereof.

2. The method of claim 1 wherein the endotoxin-mediated disorder is sepsis.

3. The method of claim 1 further comprising co-administering a modulator of an immune response.

4. The method of claim 3 wherein the modulator is a stimulator of an immune response.

5. The method of claim 4 wherein the stimulator of an immune response is a cytokine.

6. The method of claim 3 wherein the modulator is an inhibitor of an immune response.

7. The method of claim 1 wherein the symptom is acute lung injury.

8. The method of claim 1 wherein the endotoxin-mediated disorder is selected from the group comprising multi-organ dysfunction syndrome (MODS), kidney failure, and liver failure.

* * * * *

SEQUENCE LISTING

```
<160> NUMBER OF SEQ ID NOS: 2

<210> SEQ ID NO 1
<211> LENGTH: 982
<212> TYPE: PRT
<213> ORGANISM: Homo sapiens

<400> SEQUENCE: 1

Met Ala Asn Ser Met Asn Gly Arg Asn Pro Gly Gly Arg Gly Gly Asn
1               5                   10                  15

Pro Arg Lys Gly Arg Ile Leu Gly Ile Ile Asp Ala Ile Gln Asp Ala
            20                  25                  30

Val Gly Pro Pro Lys Gln Ala Ala Ala Asp Arg Arg Thr Val Glu Lys
        35                  40                  45

Thr Trp Lys Leu Met Asp Lys Val Val Arg Leu Cys Gln Asn Pro Lys
    50                  55                  60

Leu Gln Leu Lys Asn Ser Pro Pro Tyr Ile Leu Asp Ile Leu Pro Asp
65                  70                  75                  80

Thr Tyr Gln His Leu Arg Leu Ile Leu Ser Lys Tyr Asp Asp Asn Gln
                85                  90                  95
```

```
Lys Leu Ala Gln Leu Ser Glu Asn Glu Tyr Phe Lys Ile Tyr Ile Asp
            100                 105                 110
Ser Leu Met Lys Lys Ser Lys Arg Ala Ile Arg Leu Phe Lys Glu Gly
            115                 120                 125
Lys Glu Arg Met Tyr Glu Glu Gln Ser Gln Asp Arg Arg Asn Leu Thr
        130                 135                 140
Lys Leu Ser Leu Ile Phe Ser His Met Leu Ala Glu Ile Lys Ala Ile
145                 150                 155                 160
Phe Pro Asn Gly Gln Phe Gln Gly Asp Asn Phe Arg Ile Thr Lys Ala
                165                 170                 175
Asp Ala Ala Glu Phe Trp Arg Lys Phe Phe Gly Asp Lys Thr Ile Val
                180                 185                 190
Pro Trp Lys Val Phe Arg Gln Cys Leu His Glu Val His Gln Ile Ser
            195                 200                 205
Ser Gly Leu Glu Ala Met Ala Leu Lys Ser Thr Ile Asp Leu Thr Cys
        210                 215                 220
Asn Asp Tyr Ile Ser Val Phe Glu Phe Asp Ile Phe Thr Arg Leu Phe
225                 230                 235                 240
Gln Pro Trp Gly Ser Ile Leu Arg Asn Trp Asn Phe Leu Ala Val Thr
                245                 250                 255
His Pro Gly Tyr Met Ala Phe Leu Thr Tyr Asp Glu Val Lys Ala Arg
                260                 265                 270
Leu Gln Lys Tyr Ser Thr Lys Pro Gly Ser Tyr Ile Phe Arg Leu Ser
            275                 280                 285
Cys Thr Arg Leu Gly Gln Trp Ala Ile Gly Tyr Val Thr Gly Asp Gly
        290                 295                 300
Asn Ile Leu Gln Thr Ile Pro His Asn Lys Pro Leu Phe Gln Ala Leu
305                 310                 315                 320
Ile Asp Gly Ser Arg Glu Gly Phe Tyr Leu Tyr Pro Asp Gly Arg Ser
                325                 330                 335
Tyr Asn Pro Asp Leu Thr Gly Leu Cys Glu Pro Thr Pro His Asp His
                340                 345                 350
Ile Lys Val Thr Gln Glu Gln Tyr Glu Leu Tyr Cys Glu Met Gly Ser
            355                 360                 365
Thr Phe Gln Leu Cys Lys Ile Cys Ala Glu Asn Asp Lys Asp Val Lys
        370                 375                 380
Ile Glu Pro Cys Gly His Leu Met Cys Thr Ser Cys Leu Thr Ala Trp
385                 390                 395                 400
Gln Glu Ser Asp Gly Gln Gly Cys Pro Phe Cys Arg Cys Glu Ile Lys
                405                 410                 415
Gly Thr Glu Pro Ile Ile Val Asp Pro Phe Asp Pro Arg Asp Glu Gly
            420                 425                 430
Ser Arg Cys Cys Ser Ile Ile Asp Pro Phe Gly Met Pro Met Leu Asp
        435                 440                 445
Leu Asp Asp Asp Asp Asp Arg Glu Glu Ser Leu Met Met Asn Arg Leu
450                 455                 460
Ala Asn Val Arg Lys Cys Thr Asp Arg Gln Asn Ser Pro Val Thr Ser
465                 470                 475                 480
Pro Gly Ser Ser Pro Leu Ala Gln Arg Arg Lys Pro Gln Pro Asp Pro
                485                 490                 495
Leu Gln Ile Pro His Leu Ser Leu Pro Pro Val Pro Pro Arg Leu Asp
            500                 505                 510
Leu Ile Gln Lys Gly Ile Val Arg Ser Pro Cys Gly Ser Pro Thr Gly
```

```
                515                 520                 525
Ser Pro Lys Ser Ser Pro Cys Met Val Arg Lys Gln Asp Lys Pro Leu
    530                 535                 540

Pro Ala Pro Pro Pro Leu Arg Asp Pro Pro Pro Pro Pro Glu
545                 550                 555                 560

Arg Pro Pro Pro Ile Pro Pro Asp Asn Arg Leu Ser Arg His Ile His
                565                 570                 575

His Val Glu Ser Val Pro Ser Arg Asp Pro Pro Met Pro Leu Glu Ala
            580                 585                 590

Trp Cys Pro Arg Asp Val Phe Gly Thr Asn Gln Leu Val Gly Cys Arg
        595                 600                 605

Leu Leu Gly Glu Gly Ser Pro Lys Pro Gly Ile Thr Ala Ser Ser Asn
    610                 615                 620

Val Asn Gly Arg His Ser Arg Val Gly Ser Asp Pro Val Leu Met Arg
625                 630                 635                 640

Lys His Arg Arg His Asp Leu Pro Leu Glu Gly Ala Lys Val Phe Ser
                645                 650                 655

Asn Gly His Leu Gly Ser Glu Glu Tyr Asp Val Pro Pro Arg Leu Ser
            660                 665                 670

Pro Pro Pro Pro Val Thr Thr Leu Leu Pro Ser Ile Lys Cys Thr Gly
        675                 680                 685

Pro Leu Ala Asn Ser Leu Ser Glu Lys Thr Arg Asp Pro Val Glu Glu
    690                 695                 700

Asp Asp Asp Glu Tyr Lys Ile Pro Ser Ser His Pro Val Ser Leu Asn
705                 710                 715                 720

Ser Gln Pro Ser His Cys His Asn Val Lys Pro Pro Val Arg Ser Cys
                725                 730                 735

Asp Asn Gly His Cys Met Leu Asn Gly Thr His Gly Pro Ser Ser Glu
            740                 745                 750

Lys Lys Ser Asn Ile Pro Asp Leu Ser Ile Tyr Leu Lys Gly Asp Val
        755                 760                 765

Phe Asp Ser Ala Ser Asp Pro Val Pro Leu Pro Pro Ala Arg Pro Pro
    770                 775                 780

Thr Arg Asp Asn Pro Lys His Gly Ser Ser Leu Asn Arg Thr Pro Ser
785                 790                 795                 800

Asp Tyr Asp Leu Leu Ile Pro Pro Leu Gly Glu Asp Ala Phe Asp Ala
                805                 810                 815

Leu Pro Pro Ser Leu Pro Pro Pro Pro Ala Arg His Ser Leu
            820                 825                 830

Ile Glu His Ser Lys Pro Pro Gly Ser Ser Arg Pro Ser Ser Gly
        835                 840                 845

Gln Asp Leu Phe Leu Leu Pro Ser Asp Pro Phe Val Asp Leu Ala Ser
    850                 855                 860

Gly Gln Val Pro Leu Pro Pro Ala Arg Arg Leu Pro Gly Glu Asn Val
865                 870                 875                 880

Lys Thr Asn Arg Thr Ser Gln Asp Tyr Asp Gln Leu Pro Ser Cys Ser
                885                 890                 895

Asp Gly Ser Gln Ala Pro Ala Arg Pro Pro Lys Pro Arg Pro Arg Arg
            900                 905                 910

Thr Ala Pro Glu Ile His His Arg Lys Pro His Gly Pro Glu Ala Ala
        915                 920                 925

Leu Glu Asn Val Asp Ala Lys Ile Ala Lys Leu Met Gly Glu Gly Tyr
    930                 935                 940
```

```
Ala Phe Glu Glu Val Lys Arg Ala Leu Glu Ile Ala Gln Asn Asn Val
945                 950                 955                 960

Glu Val Ala Arg Ser Ile Leu Arg Glu Phe Ala Phe Pro Pro Pro Val
                965                 970                 975

Ser Pro Arg Leu Asn Leu
            980

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
agttgagggg actttcccag gc                                           22
```